United States Patent [19]
Geiges, Jr.

[11] Patent Number: 5,830,231
[45] Date of Patent: Nov. 3, 1998

[54] HANDLE AND ACTUATING MECHANISM FOR SURGICAL INSTRUMENTS

[76] Inventor: John J. Geiges, Jr., 4143 Sebago Rd., Yonges Island, S.C. 29449

[21] Appl. No.: 821,667

[22] Filed: Mar. 19, 1997

[51] Int. Cl.⁶ .................................................. A61B 17/28
[52] U.S. Cl. .............................. 606/205; 606/1; 606/119; 606/139; 606/140; 606/142; 606/144; 606/167; 606/170; 606/174; 606/205; 606/206; 606/207; 606/208; 606/188
[58] Field of Search ................................ 606/1, 119, 139, 606/140, 142, 144, 167, 170, 174, 205, 206, 207, 208, 188

[56] References Cited

U.S. PATENT DOCUMENTS

| | | | |
|---|---|---|---|
| 5,480,409 | 1/1996 | Riza | 606/205 |
| 5,562,694 | 10/1996 | Morcellator | 606/176 |
| 5,626,608 | 5/1997 | Cuny et al. | 606/205 |

*Primary Examiner*—Michael Powell Buiz
*Assistant Examiner*—Vy Q. Bui
*Attorney, Agent, or Firm*—Clifton Ted Hunt

[57] ABSTRACT

This invention relates to surgical tools and more specifically to a modular handle and modular actuating mechanism for a group of working tips or tools, such as scissors, forceps and clamps used in open surgery or inserted within a patient's body during an endoscopy or laparoscopy. The handle is ergonomical.

11 Claims, 5 Drawing Sheets

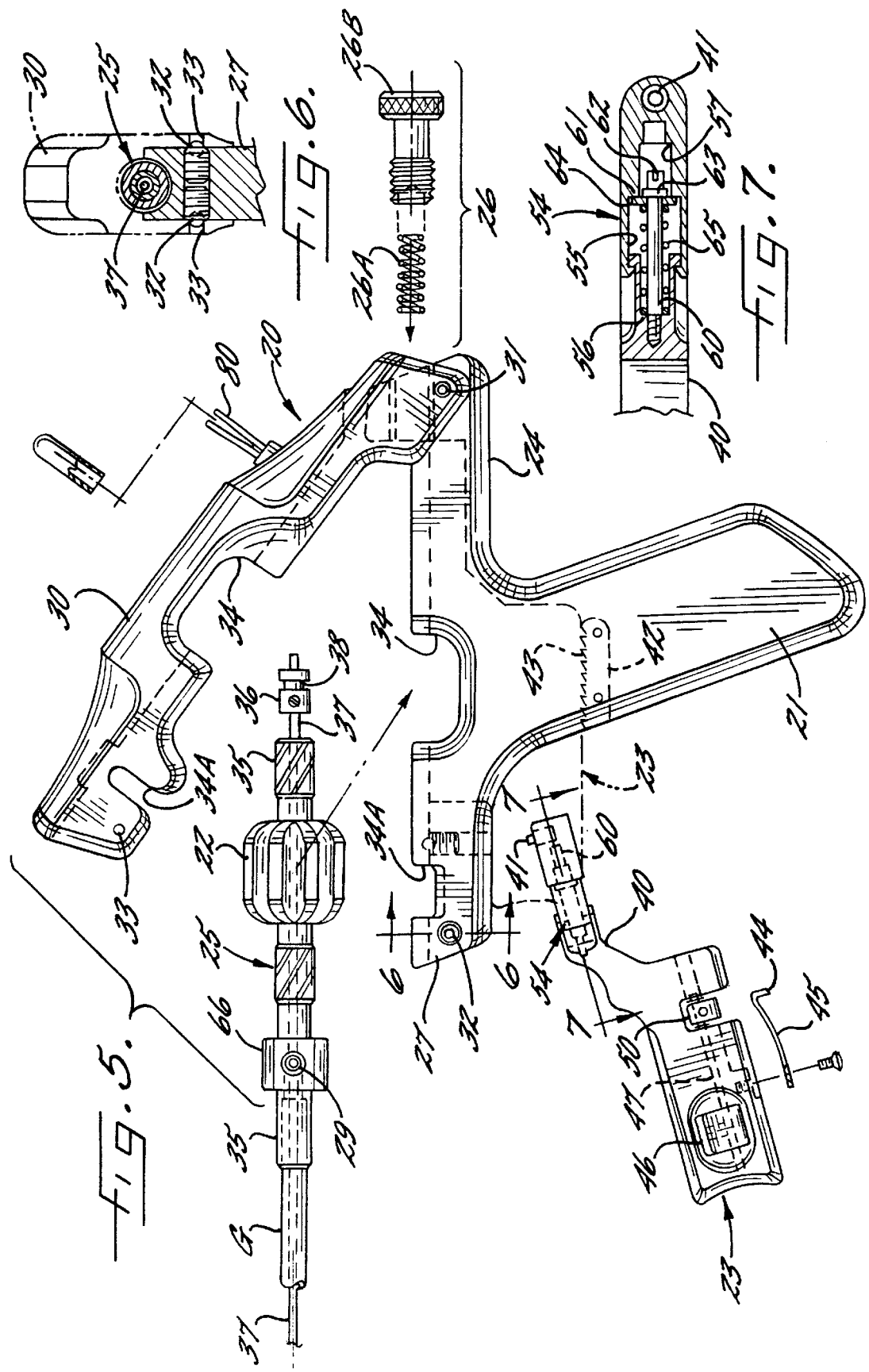

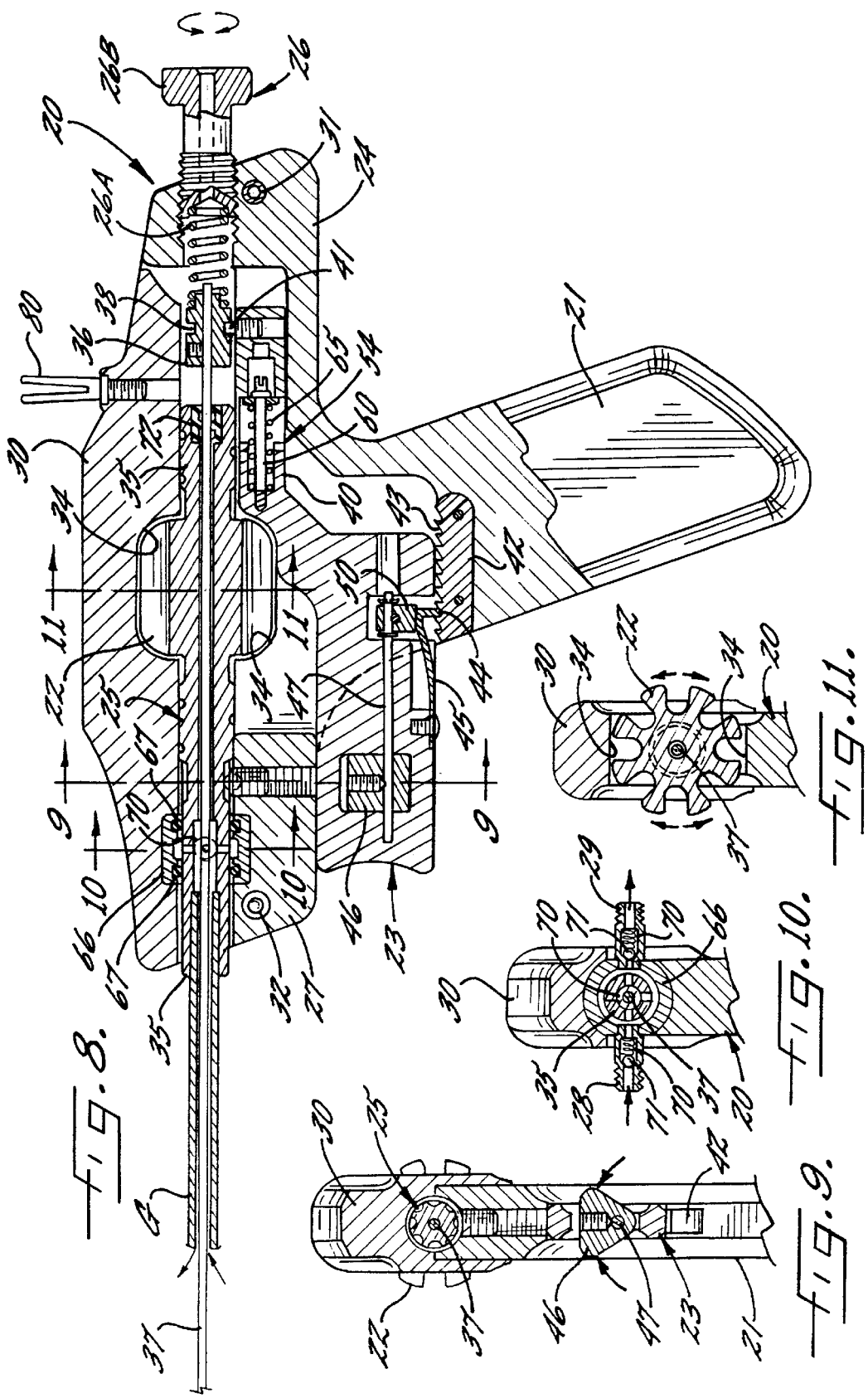

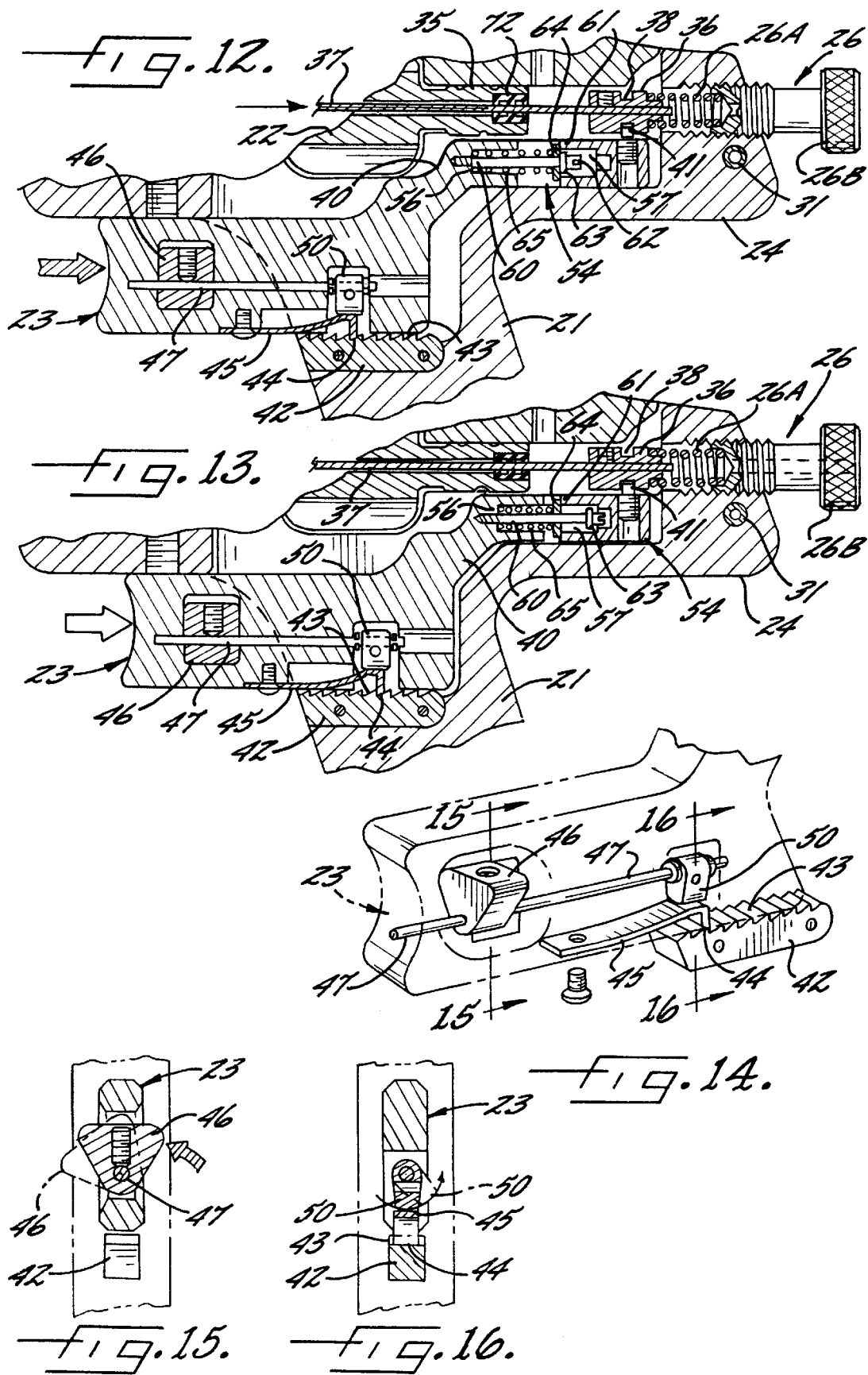

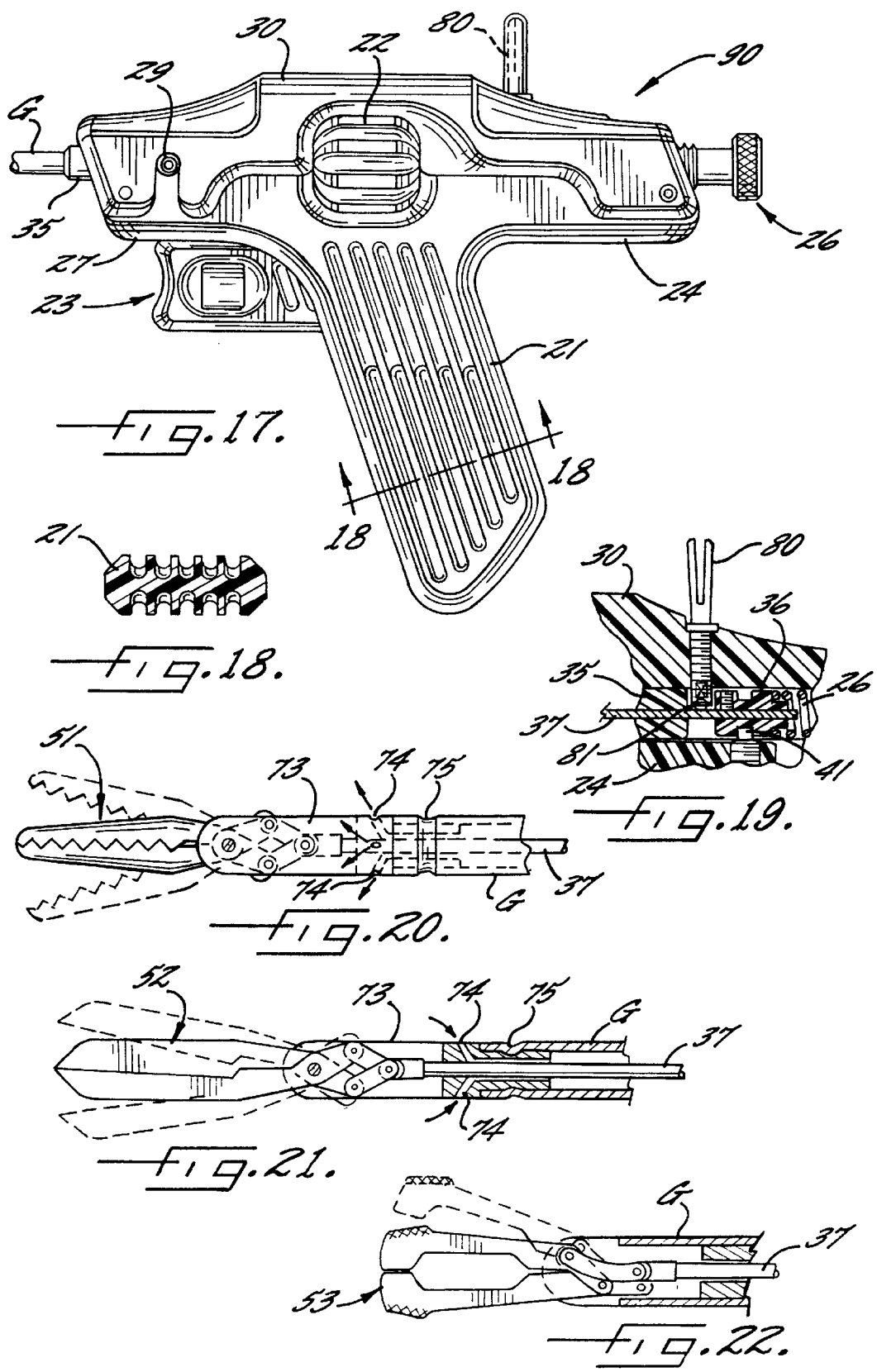

HANDLE AND ACTUATING MECHANISM FOR SURGICAL INSTRUMENTS

FIELD OF THE INVENTION

This invention relates to surgical instruments and more specifically to the actuating mechanism for a group of working tips or tools, such as scissors, forceps and clamps used in open surgery or inserted within a patient's body during an endoscopy or laparoscopy.

BACKGROUND OF THE INVENTION

The practice of endoscopic and laparoscopic or minimally-invasive surgery is becoming more widely used because it is less traumatic than conventional open surgery. With endoscopic and laparoscopic surgery, only a relatively tiny incision is required, thus reducing the time for healing and consequently reducing the length of hospitalization and costs, as well as minimizing patient discomfort.

The relatively tiny incision is made to accommodate a cannula, which in turn accommodates a slender rod that is operably connected to an apparatus in the handle at the proximal end and to the working tips or tools at the distal end. The apparatus is responsive to movement of a surgeon's hand on the handle to actuate a tool at the distal end of the cannula. The cannula and working tips may extend only a fraction of an inch from the handle for open surgery or may extend several inches for the working tips to extend within a patient's body during an endoscopy or laparoscopy. The tools are specially configured to grasp, manipulate or cut tissue within a patient responsive to the position or motion of the surgeon's hand on the handle.

There are several actuating mechanisms for the working tips in the prior art. Most of them are awkward to handle over a long period of time because they require awkward movement of the surgeon's thumb. None of the prior art mechanisms provide the surgeon with the comfort that is desirable for the surgeon to maintain uniform efficiency during a long operation. See, for example, the scissors-like grip in the following patents:

| Number | Date | Inventor | Title |
| --- | --- | --- | --- |
| 5,209,747 | May 11, 1993 | Knoepfler | ADJUSTABLE ANGLE MEDICAL FORCEPS |
| 5,275,614 | Jan 4, 1994 | Haber et al. | AXIALLY EXTENDABLE ENDOSCOPIC SURGICAL INSTRUMENT |
| 5,300,087 | Apr 5, 1994 | Knoepfler | MULTIPLE PURPOSE FORCEPS |
| 5,304,203 | Apr 19, 1994 | Eli-Mallawany | TISSUE EXTRACTING FORCEPS FOR LAPAROSCOPIC SURGERY |

The scissors-like grip disclosed in the foregoing patents is widely used but it is not structured to satisfactorily impart the desired actuation or clamping to the working tip, because of the uncomfortable stress it places on the surgeon's hand. The same is true of many of the so-called "pistol grips" that are being used on the proximal end of both open and laparoscopic surgical instruments. See, for example, the following patents:

| Number | Date | Inventor | Title |
| --- | --- | --- | --- |
| 5,300,082 | Apr 5, 1994 | Sharps et al. | ENDONEEDLE HOLDER SURGICAL INSTRUMENT |
| 5,458,598 | Oct 17, 1995 | Feinberg et al. | CUTTING AND COAGULATING FORCEPS |
| 5,480,409 | Jan 2, 1996 | Riza | LAPAROSCOPIC SURGICAL INSTRUMENT |
| 5,562,655 | Oct 8, 1996 | Mittelstadt | SURGICAL APPARATUS HAVING A UNIVERSAL HANDLE FOR ACTUATING VARIOUS ATTACHMENTS |
| 5,562,694 | Oct 8, 1996 | Sauer et al. | MORCELLATOR |

The pistol grips disclosed in these patents, and in others, have been designed to encompass mechanical concepts for operating the working tip instead of being configured for specific reduction in hand fatigue and increased stability and efficiency in the surgeon's control of the working tip.

SUMMARY OF THE INVENTION

It is an object of this invention to provide a comfortable handle to minimize the manual fatigue encountered by surgeons during long operations.

It is another object of the invention to provide a modular reusable actuating mechanism with a minimum of parts that can be easily taken apart without tools for cleaning or replacement of parts.

Another object of the invention is to provide an actuating mechanism with controls for the mechanism located on the handle within easy reach of the index finger and thumb of the same hand that holds the handle.

Still another object of the invention is to integrate working tips, such as scissors, clamps, needle drivers and retractors with their own cannulas within novel cartridge modules. Working tips are thereby readily replaced as needed during surgery by simply opening the handle to lift out the cartridge module with one working tip and drop in the cartridge module with a selected working tip. The handle is then closed about the cartridge module with the selected working tip to retain it in operable position for use.

A further object of the invention is to provide a dual function, telescopic sliding trigger accessible by the surgeon's index finger to comfortably and accurately control the working tip. A ratchet firmly locks the trigger when desired.

Another object of the invention is to provide a roul with 360° indexed rotation that controls the rotation of the working tip and is easily accessed by the thumb on the surgeon's hand that holds the handle.

Still another object of the invention is the provision of suction/irrigation capability through the cannula without use of tubing in the cannula. The roul is also used to direct the suction and irrigation capabilities of the tool.

Other objects of the invention will become apparent when reading the following description of the invention in conjunction with the accompanying drawings.

BRIEF DESCRIPTION OF THE DRAWINGS

FIG. 5 is an exploded side view illustrating the components of the invention and the opening of the handle;

FIG. 6 is a vertical sectional view taken substantially along the line 6—6 in FIG. 5;

FIG. 7 is a sectional view taken substantially along the line 7—7 in FIG. 5;

FIG. 8 is a sectional view of the housing and actuating mechanism;

FIG. 9 is a sectional view taken substantially along the line 9—9 in FIG. 8;

FIG. 10 is a sectional view taken substantially along the line 10—10 in FIG. 8;

FIG. 11 is a sectional view taken substantially along the line 11—11 in FIG. 8;

FIG. 12 and 13 are enlarged sectional views, with parts broken away, of the trigger and the rearward extension of the handle, illustrating use of the telescopic connection that enables long strokes of the trigger;

FIG. 14 is an enlarged perspective view of the trigger and ratchet;

FIG. 15 is a sectional view taken substantially along the line 15—15 in FIG. 14;

FIG. 16 is a sectional view taken substantially along the line 16—16 in FIG. 14;

FIG. 17 is a perspective view of an alternate embodiment of the invention, wherein the handle is made of plastic;

FIG. 18 is sectional view taken substantially along the line 18—18 in FIG. 17;

FIG. 19 is a sectional view illustrating the cautery terminal in the plastic handle of FIG. 18; and FIGS. 20, 21 and 22 are side views illustrating different tools with which the handle and actuating mechanism of this invention are used, namely a clamp (FIG. 20), scissors (FIG. 21) and a retractor (FIG. 22).

DETAILED DESCRIPTION OF THE INVENTION

Ergonomics

Figure 1:
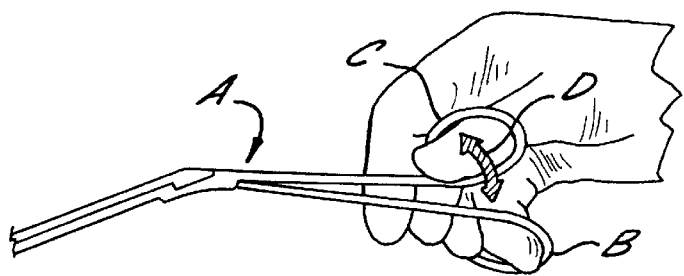
FIG. 1 and 2 are side views illustrating the use of prior art handles for surgical instruments.

FIG. 1 shows a prior art scissors-type handle A that is currently used by many surgeons. The handle A has a loop B for the fingers and a loop C for the thumb. As indicated by the arrow D, the implement is actuated by repetitive and tiresome movement of the thumb.

Figure 2:
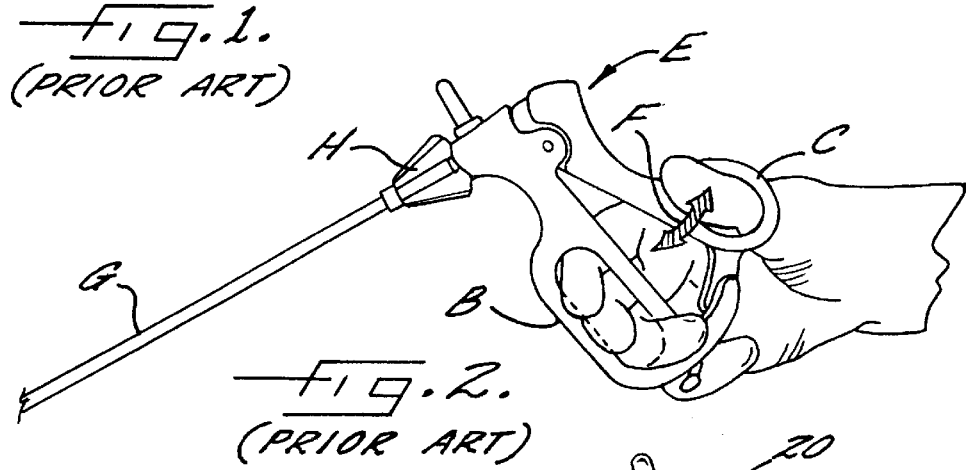

FIG. 2 shows another prior art scissors-type handle E that is currently used by many surgeons. Like the handle A, the handle E has a loop B for the fingers and a loop C for the thumb. A is indicated by the arrow F, the implement shown in FIG. 2 is also actuated by repetitive and tiresome movement of the thumb. A cannula G is operatively connected to a roul H extending from the handle E in FIG. 2. The roul H is manipulated to rotate working tips (not shown) at the end of the cannula in a known manner. As clearly shown in FIG. 2, manipulation of the roul H cannot be accomplished by the same hand that holds the handle E.

Figure 3:
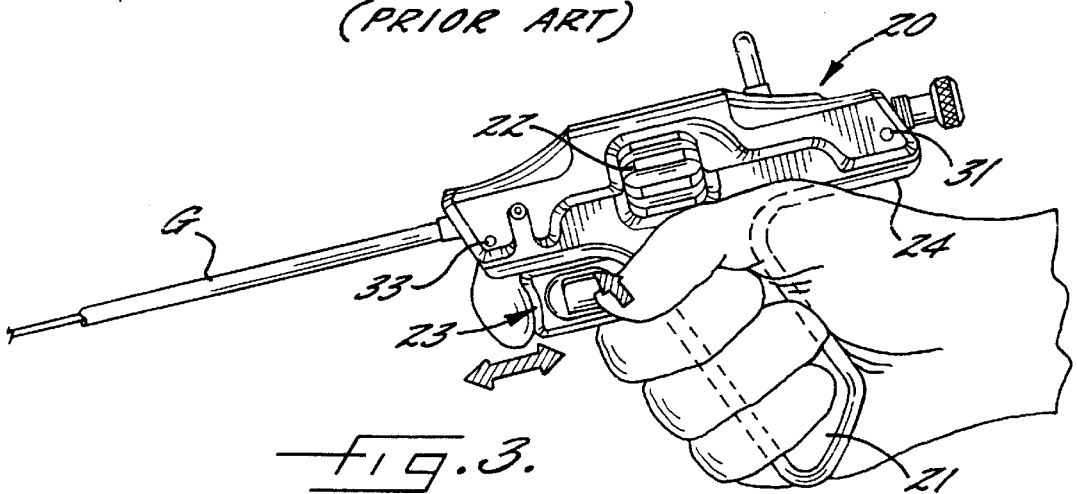
FIG. 3 and 4 are side views illustrating the use of the handle of this invention.
Figure 4:
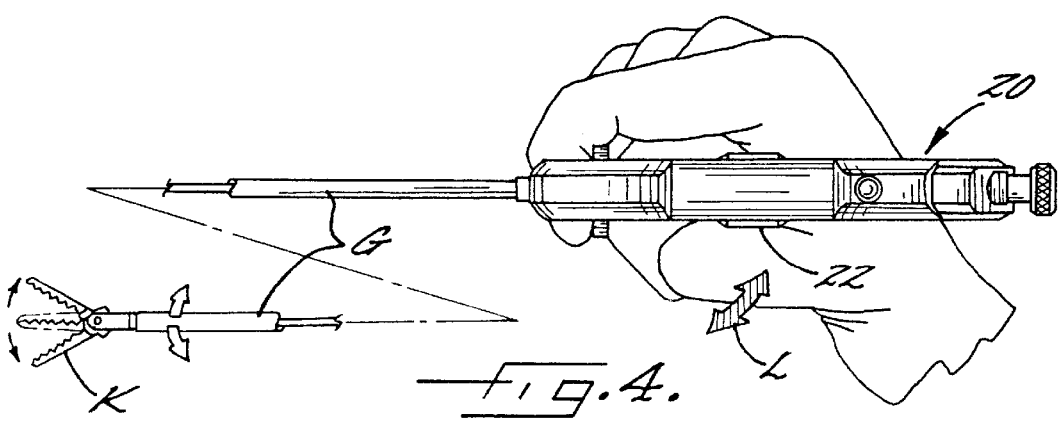

The ergonomic disadvantages of the prior art are overcome by the present invention. FIGS. 3 and 4 illustrate that the shape, width and breadth of the handle 20 in the present invention comfortably conforms with the angle created by the human hand in its relaxed position with the index finger extended. A grip 21 on the handle is held between the three fingers and the palm of the hand, leaving the thumb and index finger free to operate a roul 22 and trigger 23 of the actuating mechanism. An extension 24 of the handle extends rearwardly at an acute angle from the grip 21 to permit the handle 20 to be cradled in the web between the thumb and index finger of the surgeon, and to place the longitudinal axis of the cannula in close proximity to the operative plane of the surgeon's forearm and wrist when using the apparatus. Another advantage of the rearward extension of the handle is that its weight and mass provides a "balanced feel" which minimizes muscle fatigue in the surgeon's hand.

Working tips at the end of the cannula G, such as a clamp K, are closed by pressing against the trigger 23 with the index finger, and are opened by releasing pressure on the trigger. The roul 22 rotates the working tips as desired and is located in close proximity to the user's thumb, as shown in FIG. 3. FIG. 4 illustrates that the roul can be easily manipulated by up and down movement of the thumb, as indicated by the arrow L.

Structure

Referring to FIG. 5, it will be seen that the modular handle and actuating mechanism of the present invention comprises four individual modules: the handle 20, the trigger 23, a cartridge module 25 and a spring assembly 26. The modules may be made of metal and be replaceable or made from plastic and be disposable.

The Handle

In addition to the grip 21 and rearward extension 24, the handle 20 comprises a forward extension 27 and a cover 30. The forward extension 27 is aligned with the rearward extension 24 and extends forwardly at an obtuse angle from the grip 21. The cover 30 is hinged as at 31 to the rear extension 24 and, when closed, extends over the rear extension 24, the grip 21 and the forward extension 27. The cover 30 is releasably held in the closed and operative position of FIG. 3 by spring pressed detents 32 (FIG. 6) extending outwardly from the forward extension 27 into opposed openings 33 in the cover 30. The user moves the cover 30 to the open position of FIG. 5 to either clean the apparatus or to install or remove a cartridge module 25. The cover is opened by simply grasping the cover in one hand and the forward extension 27 in the other hand and pulling them apart to pivot the cover about its hinged connection 31 to the rear extension 24.

The spring assembly 26 comprises a spring 26A and a threaded adjustment rod 26B. The rod 26B is threaded into the end of the rearward extension 24 at the time of manufacture to press the spring 26A against the proximal end of the cartridge module 25 in the handle. The tension of the spring 26A can be adjusted by rotating the rod 26B. The rod 26B need not be normally removed from the handle.

The top of the forward extension 27 and the inner surface of the cover 30 are shaped to conform with that portion of the cartridge module 25 that extends between them. The cover and the top of the grip are cut away as at 34 to receive the roul 22, and at 34A to receive irrigation and suction ports 28 and 29 (FIG. 10). The installed cartridge module 25 extends beyond the cut away portions 34 and terminates in the rearward extension 24.

The Cartridge Module

The cartridge module 25 comprises the roul 22, a rout spindle 35, the cannula G and a transfer cylinder 36, all of which are interconnected to form the cartridge module 25 as an integral unit. There are the usual tools at the distal end of the cannula G operated by a rod 37 extending through the cannula in the usual manner. The rod 37 extends through the cartridge module and terminates in the rearward extension 24 after being fastened to the transfer cylinder 36 near its proximal end. The transfer cylinder 36 has an annular groove 38 that serves a function in providing an operable connection between the rod 37 and the trigger 23.

According to the invention, a plurality of cartridge modules 25 will be provided with each handle 20. The cartridge modules will be equipped with different tools and will be preferably color coded to identify the different tools, such as red for a cartridge module with scissors and blue for a cartridge module with a clamp.

Different tools can be operatively connected to the trigger 23 by simply opening the cover and dropping a desired color of cartridge module in the handle and closing the cover, all without the use of tools. The relative ease and speed with which selected tools can be operably installed in the handle enables a surgical team to efficiently perform at a fast pace with little or no down time.

The Trigger

The trigger 23 is a modular sliding trigger. It is slidably received in the grip 21 and is not connected to the handle. The trigger 23 includes a spur 40 which extends into the rearward extension 24. Finger pressure on the trigger 23 causes the trigger to slide rearwardly within the grip 21 and causes corresponding rearward movement of the spur 40 in the rearward extension 24. An actuating pin 41 rises from the spur to register with the annular groove 38 in the transfer cylinder and thereby operably connect the trigger 23 to the tool at the distal end of the rod 37. Pressure on the trigger moves the rod 37 rearwardly. When rearward pressure is removed from the trigger 23, the adjustable tension spring 26 tends to return the rod to its forward or normal position.

It is desirable to retain pressure on the trigger in some instances, as when tightly closing a clamp about tissue to be removed during a laparoscopic or endoscopic procedure. For this purpose, the trigger 23 traverses a ratchet 42 embedded in the grip beneath the path of the trigger. The ratchet is serrated with rearwardly facing teeth 43 which are successively engaged by the down turned end 44 of a leaf spring 45 fastened to the bottom of the trigger 23 (FIG. 8). A locking lever 46 extends transversely through the medial portion of the trigger and is connected by a shaft 47 extending through that portion of the trigger that overlies the leaf spring 45 to a locking cam 50 above the down turned end 44 of the leaf spring 45. The trigger may be retained in a retracted position without finger pressure by manipulation of the locking lever 46 to rotate the locking cam 50 into engagement with the leaf spring and thereby hold the down turned end 44 of the leaf spring behind one of the rearwardly facing teeth 43 on the ratchet 42.

Different amounts of finger pressure on the trigger are required for the different tools that are on the distal ends of the rods 37 in different cartridge modules 25. Examples of the different tools are illustrated in FIGS. 20–22. FIG. 20 shows a clamp 51; FIG. 21 shows scissors 52; and FIG. 22 shows a retractor 53. The linkage of the tools 51–53 to the rod 37 is conventional and a description thereof is deemed unnecessary.

The repetitive manipulation of the scissors 52 by short strokes of the trigger to cut tissue generally requires less finger pressure on the trigger than does the removal of tissue or other body part by the tight closing of the clamps 51 with a single long stroke of the trigger. Cutting of tissue with scissors necessitates the use of short strokes because the small movement of the scissor blades on each stroke permits only a short stroke of the trigger. It is not possible to tightly clamp tissue with only a short stroke of the trigger because a long stroke of the trigger is required to transmit the requisite holding power to the clamp at the distal end of the cannula.

A shock absorber, broadly indicated at 54 in FIGS. 7, 12 and 13, is installed in the spur 40 between the trigger 23 and the actuating pin 41. The shock absorber 54 comprises an elongated chamber 55 having a forward end 56 and a rearward end 57 within the spur 40. A guide pin 60 is threaded into the spur 40 at the forward end 56 of the chamber 55 and the guide pin 60 extends rearwardly beyond an annular abutment 61 that extends radially into the chamber 55. The rearward end of the guide pin 60 is knurled or slotted as at 62 to facilitate the threaded insertion of the guide pin in the spur 40 at the forward end 56 of the chamber. A flange 63 extends radially from the guide pin 60 near its rearward end 57. A stop washer 64 surrounds the guide pin 60 and seats against the annular abutment 61. A coiled spring 65 surrounds the guide pin 60 and extends between the forward end 56 of the chamber 55 and the stop washer 64.

The spring 65 is stronger than the adjustable tension spring 26 that bears against the transfer cylinder 36 at the proximal end of the rod 37. Light finger pressure against the trigger 37, as when operating scissors 52, does not compress the spring 65 in the shock absorber 54 but is transmitted to the actuating pin 41 and the transfer cylinder to compress the spring 26 and move the rod 37 rearwardly, as illustrated in FIG. 12. Heavy finger pressure against the trigger 37, as when using the clamp 51, does compress the spring 65 in the shock absorber 54, and in so doing enables a long stroke of the trigger 23. The relative positions of the down turned leaf spring end 44 on the ratchet 42 in FIGS. 12 and 13 illustrate the increased length of the stroke when the shock absorber spring 65 is compressed by heavy finger pressure on the trigger 23.

Because the guide pin 60 is threaded in place within the chamber 55 and the stop washer 64 and spring 65 are installed at the time of manufacture, the trigger 23 remains modular and can be removed from the handle 20 for cleaning or repair without the use of tools.

The handle 20 is adaptable to hand size differences by manufacturing the trigger modules in different sizes. Triggers of different sizes are preferably color coded for easy identification of size.

Irrigation and Suction

In the prior art, irrigation and suction have been used with surgical tools for endoscopic and laparoscopic surgery. The fluids for both irrigation and surgery were passed through separate tubes extending through the cannula or trocar. This presents a problem because the tubes for irrigation and suction prevent the rod in the cannula or trocar from being rotated 360°.

According to the present invention, fluids for both irrigation and suction are passed through the cannula G without the use of tubes, as in the prior art. See FIGS. 8, 10, 20 and 21. FIG. 10 shows an access port 28 for connecting a tube (not shown) through which an irrigation fluid can be introduced into the cannula G. A relief port 29 is shown in opposed relation to the access port 28 for connecting a tube (not shown) through which fluids can be drawn from the patient's body and the cannula G.

The ports 28 and 29 extend through opposed notches 34A in the handle 20 and cover 30 (FIG. 5) and are journaled in a sleeve 66 that fits about the roul spindle 35 (FIG. 10). O-rings 67 provide a fluid-tight connection of the sleeve 66 with the roul spindle 35.

Each of the ports 28 and 29 comprises a manifold 70 containing a spring-pressed check valve 71. The check valve 71 in the irrigation port 28 is arranged to prevent fluid from passing out through the port 28 and the check valve 71 in the suction port 29 is arranged to prevent fluid from passing in through the port 29. A labyrinth sleeve 72 is on the rod 37 in rearwardly spaced relation to the terminals 28 and 29 to prevent leakage of pressure and vacuum around the roul spindle 35, which rotates 360° around the labyrinth sleeve 72.

Fluid introduced through the irrigation port 28 passes through the roul spindle 35 and into the manifold 70 which communicates with the cannula G. The irrigation fluid continues through the cannula G and around the rod 37 to a pivot housing 73 at the end of the cannula G. The pivot housing 73 has openings 74 communicating with the cannula G, the openings 74 serving as outlets for irrigation as indicated in FIG. 20 or as inlets for suction as indicated in FIG. 21.

The pivot housing 73 is swaged onto the cannula as at 75 (FIGS. 20 and 21) with the operating rod 37 extending through the pivot housing to the working tip or tool (such as indicated at 51 and 52 in FIGS. 20 and 21).

Cauterizing

A cauterizing terminal 80 extends upwardly from the cover 30 in the metal embodiment of FIG. 5 and in the plastic embodiment of FIG. 17. In the metal embodiment of FIG. 5, the cauterizing current is carried to the working tips in the usual manner and a description thereof is deemed unnecessary.

In the plastic embodiment of FIG. 17 the cauterizing terminal 80 is threaded into the plastic cover 30 and extends through the cover into a space between the roul spindle 35. A spring-pressed detent 81 extends from the threaded inner tip of the terminal 80 to engage the rotatable rod 37.

Conclusion

There is thus provide a novel handle that is comfortable when handling surgical instruments and that releasably encloses an actuating mechanism for surgical instruments that is simple and easy to operate for efficient use during open surgery, endoscopic surgery and laparoscopic surgery.

I claim:

1. A modular apparatus for surgical instruments, said apparatus comprising a modular handle, a modular trigger and a cartridge module, and the modular trigger and the cartridge module being operably interconnected in the modular handle.

2. An ergonomically designed handle that houses an actuating mechanism for surgical instruments wherein the ergonomical handle comprises a grip, a rearward extension extending at an acute angle from the grip, a forward extension extending in alignment with the rearward extension and at an obtuse angle from the grip, a cover overlying the forward extension, the grip and the rearward extension, means pivotally attaching the cover to the rearward extension, and means releasably connecting the cover to the forward extension.

3. The invention of claim 2 wherein the actuating mechanism comprises a cartridge module, a modular trigger and an adjustable tension spring assembly including a transfer cylinder, the cartridge module comprising a roul spindle extending through the forward extension and into the rearward extension, a cannula fixed to the end of the spindle extending from the forward extension, the cannula having a reciprocable rod extending therethrough, the rod having a tool fixed to its distal end and the transfer cylinder fixed to its proximal end, the modular trigger including a spur and being slidably received in the grip and rearward extension of the handle, and means connecting the trigger to the transfer cylinder, whereby pressure on the trigger is transmitted to the tool on the distal end of the rod, and whereby no special tools are required by the user for assembling and disassembling the actuating mechanism.

4. The invention of claim 3 wherein the means connecting the trigger to the transfer cylinder is an actuating adaptor extending from the spur of the trigger.

5. In an actuating mechanism for surgical tools, a cartridge module comprising a roul, a roul spindle, a cannula, an operating rod mounted for rotation within the cannula, and a working tip at the distal end of the cappula.

6. The invention of claim 5 wherein the actuating mechanism includes a handle, and means for dropping successive cartridge modules into operative position within the handle and lifting successive cartridge modules from the handle without the use of tools.

7. The invention of claim 5 wherein there are a plurality of cartridge modules with a variety of working tips, and wherein each cartridge module is color coded to identity its working tip.

8. In a handle and actuating mechanism for surgical tools wherein the handle comprises a grip and a rearward extension and the actuating mechanism includes an operating rod, a working tip at the distal end of the operating rod, a transfer cylinder at the proximal end of the operating rod, a tension spring normally urging the transfer cylinder forwardly, a sliding trigger, the trigger extending forwardly from the grip and including a spur extending into the rearward extension, an actuating pin for engagement with the transfer cylinder whereby finger pressure on the trigger overcomes the tension spring and moves the operating rod rearwardly, a ratchet, means for engaging the trigger with the ratchet to prevent forward movement of the trigger, and a shock absorber between the trigger and the transfer cylinder, whereby light and heavy finger pressure on the trigger is transmitted through the shock absorber to the transfer cylinder to move the operating rod rearwardly but heavy finger pressure on the trigger is absorbed by the shock absorber to permit a long stroke of the trigger.

9. The invention of claim 8 which includes a cauterizing terminal.

10. In the handle of claim 1 and actuating mechanism for surgical tools wherein the handle comprises a grip, a rearward extension, a forward extension and a cover and the actuating mechanism includes a cannula, an operating rod and a working tip at the distal end of the operating rod, a roul and a roul spindle, an irrigating and suction apparatus comprising an inlet portion for irrigation and an outlet portion for suction, means directing fluid for irrigation and suction into and through the cannula independently of tubes in the cannula, and means for rotating the roul spindle and the operating rod 360°.

11. The invention of claim 10 which includes a cauterizing terminal.

* * * * *